United States Patent [19]
Dennis et al.

[11] Patent Number: 5,169,638
[45] Date of Patent: Dec. 8, 1992

[54] BUOYANT CONTROLLED RELEASE POWDER FORMULATION

[75] Inventors: Andrew Dennis; Peter Timmins, both of Merseyside; Kevin Lee, Cheshire, all of England

[73] Assignee: E. R. Squibb & Sons, Inc., Princeton, N.J.

[21] Appl. No.: 781,620

[22] Filed: Oct. 23, 1991

[51] Int. Cl.$^5$ .............................................. A61K 9/52
[52] U.S. Cl. ...................................... 424/457; 424/452;
424/488; 424/489; 424/499; 514/779; 514/781;
514/962; 514/964; 514/951
[58] Field of Search ............... 424/489, 491, 492, 493,
424/496, 499, 457, 452

[56] References Cited

U.S. PATENT DOCUMENTS

| | | | |
|---|---|---|---|
| 4,101,650 | 7/1978 | Umezawa | 424/44 |
| 4,140,755 | 2/1979 | Sheth et al. | 424/21 |
| 4,167,558 | 9/1979 | Sheth et al. | 424/22 |
| 4,702,918 | 10/1987 | Ushimaru et al. | 424/461 |
| 4,792,452 | 12/1988 | Howard et al. | 424/475 |
| 4,814,178 | 3/1989 | Bolton et al. | 424/467 |
| 4,814,179 | 3/1989 | Bolton et al. | 424/467 |

OTHER PUBLICATIONS

Stockwell et al., In Vitro Evaluation of Alginate Gel System as Sustained Release Drug Delivery Systems, Journal Controlled Release, 3, (1986), pp. 167-175.
"Gel formation with Alginate", Data Sheet D1571, Alginate Industries Limited, London.
Ingani et al., Int. J. Pharm., 35, 157-164 (1987).
J. Timmermans, A. J. Moes, Int. J. Pharm., 62, 207-216 (1990).

Primary Examiner—Thurman A. Page
Assistant Examiner—James M. Spear
Attorney, Agent, or Firm—Burton Rodney

[57] ABSTRACT

A buoyant controlled release pharmaceutical powder formulation is provided which may be filled into capsules and releases a pharmaceutical of a basic character at a controlled rate regardless of the pH of the environment, which formulation includes a basic pharmaceutical, up to about 45% by weight of a pH dependent polymer which is a salt of alginic acid, such as sodium alginate, up to about 35% by weight of a pH-independent hydrocarbon gelling agent having a viscosity of up to about 100,000 centipoises in 2% solution at 20° C. and excipients.

23 Claims, 6 Drawing Sheets

BUOYANT CONTROLLED RELEASE POWDER FORMULATION

FIELD OF THE INVENTION

The present invention relates to a buoyant or floating controlled release powder formulation, preferably a powder-filled capsule, for releasing a pharmaceutical of a basic character at a controlled rate regardless of the pH of the environment and which formulation includes up to about 45% by weight of a pH dependent polymer which is a salt of a polyuronic acid such as alginic acid, and a pH independent hydrocarbon gelling agent, such as hydroxypropylmethyl cellulose.

BACKGROUND OF THE INVENTION

The use of hydroxypropylmethyl cellulose as a rate controlling hydrophilic polymer in controlled release formulations is well-documented.

A major problem associated with most existing controlled release systems containing hydroxypropylmethyl cellulose and other pH independent rate controlling polymers is that they provide no control over drug release into media of differing pH, where drug solubility is dependent upon pH.

During transit down the digestive tract different pH environments are encountered. In the stomach acidic conditions are predominant. A gradual increase in pH then occurs during transit down the small intestine. These variations are complicated by the influence of food. For example, in the fasted state the stomach is more acidic than after a meal. Consequently this may influence the release behavior of a product which is not pH independent in its performance.

In addition, variable gastric emptying times may affect dosage form performance. A drug with an absorption "window" or poor bioavailability from the lower regions of the digestive tract may not achieve an extended period of absorption. For a drug absorbed primarily in the upper small intestine rapid gastric emptying may result in an absorption spike with no prolonged pharmacokinetic profile. Similarly with poor absorption from the large intestine rapid dosage form transit will shorten the effective period of drug delivery from the formulation. To achieve the optimum extended delivery characteristics it is therefore desirable to combine retention in the stomach with additional pH independent release. This maximizes time of drug availability for absorption and ensures consistent release regardless of elapsed time or position in the intestine.

Alginate based systems have been proposed as oral sustained release matrix dose forms. Gel formation in these systems is governed by an interaction between calcium ions and alginic acid. "Gel Formation with Alginate", Data Sheet D1571, Alginate Industries Limited, London, discloses that "gel formation is obtained by steady and uniform release of calcium, or other cations capable of forming an insoluble alginate, into the alginate solution". Other workers (Stockwell, A. F. et al., Journal Controlled Release, 3 (1986) 167–175) have employed the calcium gelled alginate system in combination with $CO_2$ generating excipients to yield a tablet that floats on the gastric contents. Such systems are not intended to pass down the GI tract and release drug in variable pH environments.

Howard et al. U.S. Pat. No. 4,792,452 discloses a non-buoyant controlled release pharmaceutical formulation in the form of a tablet which includes a basic pharmaceutical, up to about 45% by weight of a pH dependent polymer which is a salt of alginic acid, such as sodium alginate, up to about 35% by weight of a pH independent hydrocarbon gelling agent, binder and excipients. In column 3, lines 45 to 48, Howard et al. indicate that their controlled release formulation will not float in the stomach since it is more dense than water.

The use of hydrocolloid gelling agents in floating sustained release tablet formulations is known in the art. For example, Bolton et al. U.S. Pat. No(s). 4,814,178 and 4,814,179 each disclose tablets which float in gastric fluid and which contain a hydrocolloid gelling agent, a therapeutic agent and water and in the case of U.S. Pat. No. 4,814,179, an inert oil as well.

Sheth et al. U.S. Pat. No(s). 4,140,755 and 4,167,558 each disclose tablets which are buoyant in gastric juice and contain one or more hydrophillic hydrocolloids which in contact with gastric fluid will form a gelatinous mass on the surface of the tablet, thus causing it to enlarge and acquire a bulk density of less than one. However, this provides for no control of release under different pH conditions, thus drug dissolution rate will vary according to the duration of time spent in the stomach.

Umezawa U.S. Pat. No. 4,101,650 discloses pepstatin floating minicapsules wherein pepstatin is coated on very small granules of sodium bicarbonate.

Ushimaru et al. U.S. Pat. No. 4,702,918 discloses a sustained release composition which includes a gel-forming substance such as a cellulose derivative like hydroxypropylmethyl cellulose, a polysaccharide-like alginic acid, a starch derivative, a dextran, a polypeptide, a protein, or acrylic acid or vinyl derivative, together with a fat/oil which is solid at room temperature and a pharmaceutical. The sustained release composition may be in the form of a powder-filled capsule.

Stockwell et al., J. Controlled Release, 3, 167–175 (1986), investigated alginate gel formulations which included sodium bicarbonate, the intention being that the release of carbon dioxide which occurred on contact of the formulation with gastric fluid would become entrapped in the gel network producing a buoyant system. The concept was carried further by Ingani et al., *Int. J. Pharm.*, 35, 157–164 (1987) who produced tableted and floating dosage forms of a riboflavin derivative and compared their bioavailability in vivo. It was found that the bioavailability of the floating dosage forms was increased compared to the standard system. This was considered in-direct evidence that gastric retention times were increased for the novel preparation.

Various in vivo studies have been performed using these dosage forms in order to verify the possible effects of device density upon gastric retention times. The results obtained from the various studies draw conflicting conclusions; it is likely that the effectiveness of the intragastric buoyancy process may be dependent on the particular physiological conditions and/or on the dosage form characteristics. J. Timmermans, A. J. Moes, *Int. J. Pharm.*, 62, 207–216 (1990).

DESCRIPTION OF THE INVENTION

In accordance with the present invention, a buoyant controlled release pharmaceutical formulation is provided in the form of a powder which preferably is formulated as a powder-filled capsule, and which has prolonged drug release equivalent to a tablet of similar composition, pH independence of release rate equivalent to a tablet of similar composition, and yet has floating or buoyancy properties. This is especially surprising inasmuch as until now it was not thought possible that loose powder filled capsules could perform in the same way as granulated material that had undergone compression to form tablets (as disclosed in Howard et al., U.S. Pat. No. 4,792,452), and also be buoyant so that it will float on gastric juices and thereby improve drug availability.

The buoyant controlled release powder formulation of the invention will release a pharmaceutical of a basic character at a controlled rate relatively independent of the pH of the environment such that in vivo consistent release is achieved throughout the gastrointestinal tract and will have buoyant properties so that it will have extended residence time in the stomach. This is achieved without gas generation in situ, or by the incorporation of fats or waxy solids into the matrix. Dissolution properties are also maintained essentially independent of pH without the need for calcium to effect gelation.

The controlled release pharmaceutical formulation of the invention will be in the form of a powder (having an average particle size of within the range of from about 25 to about 1000 microns, preferably from about 50 to about 400 microns, and a bulk density of within the range of from about 0.1 to about 0.8 g/cm$^3$, and preferably from about 0.15 to about 0.55 g/cm$^3$), which may be filled into a capsule and includes a pharmaceutical of a basic character; a pH-dependent polymer which is a water soluble salt of a polyuronic acid, preferably alginic acid, in an amount of up to about 45% by weight depending upon the nature of the pharmaceutical present, preferably from about 15 to about 45% by weight and more preferably from about 20 to about 35% by weight of the formulation; a pH-independent hydrocolloid gelling agent having a viscosity within the range of from about 15 to about 100,000 centipoises and preferably from about 50 to about 15,000 centipoises in 2% solution at 20° C., in an amount of up to about 35% by weight, preferably within the range of from about 5 to about 20% by weight and more preferably from about 8 to about 17% by weight of the formulation; and excipients and other conventional powder ingredients. The powder formulation of the invention will not contain calcium ions so there will be no calcium ions available to interact with the polyuronic acid salts. Additionally there will be no gas generation or incorporation of lipid materials to bring about buoyancy.

It is theorized that upon oral ingestion of the sustained release buoyant powder-filled capsules of the invention, in an acid aqueous environment, such as the stomach, water penetrates the capsule shell initiating surface hydration of the pH-independent hydrocolloid gelling agent to form a gel layer and trapping air within the less dense powder bulk to account for the buoyant behavior of the capsule. At this low pH environment alginic acid is formed from the alginate salt and this modifies the gel layer. Erosion of the gel layer gradually exposes more dry matrix that hydrates to replenish the gel layer. Drug dissolves in the gel layer and diffuses out into the surrounding aqueous environment. Some interaction between the basic drug and the polyuronic acid may also be involved.

After buoyancy is lost the dosage form is emptied from the stomach and changes in pH are encountered. During passage of the drug, contained in the form of a gelled powder plug, from the stomach down the digestive tract, the pH increases, using alginic acid as an example, this causes conversion of the acid form in the stomach to a more soluble salt. The gelling agent will then be less structured and more fluid in nature. Drug can diffuse more readily through the gel layer now and the ensuing increase in release rate from the matrix compensates for the reducing driving force for dissolution at the elevated pH values, where solubility of a basic drug is lower.

The controlled release powder formulation of the invention does not contain calcium ions, or sodium bicarbonate or other carbon dioxide-producing material but it still will float in the stomach for an extended period.

The pharmaceutical of a basic character will be present in the formulation of the invention in an amount of up to about 75% by weight and preferably up to about 60% by weight.

A wide variety of medicaments (of basic nature) which are orally administered in tablet form can be used in the form of a powder prepared according to this invention. These include, for example, adrenergic agents such as salts of ephedrine, desoxyephedrine, phenylephrine, epinephrine, albuterol, fenoterol, terbutaline and the like, cholinergic agents such as salts of physostigmine, neostigmine and the like, antispasmodic agents such as salts of atropine, methantheline, papaverine and the like, tranquilizers and muscle relaxants such as salts of fluphenazine, thioridazine, trifluoperazine, chlorpromazine, triflupromazine and the like, antidepressants like salts of amitriptyline, nortriptyline, and the like, other CNS acting drugs such as BMS 181101 BMY 14,802, buspirone, nefazadone, gepirone and tiospirone, antihistamines such as salts of diphenhydramine, chlorpheniramine, dimenhydrinate, tripelennamine, perphenazine, chlorprophenazine, chlorprophenpyridamine and the like, cardioactive agents such as salts of verapamil, diltiazem, gallapomil, cinnarizine, propranolol, metoprolol, sotalol, nadolol, and salts of any of the foregoing, antimalarials such as chloroquine and the like, analgesics such as propoxyphene, meperidine and the like, etc., sympathomimetics such as salts of phenylpropanolamine and pseudoephedrine. Other therapeutic agents having the same or different physiological activity can also be employed in pharmaceutical preparations within the scope of the present invention.

The invention is particularly adapted for controlled release powder-filled capsules containing the calcium channel blocker verapamil (usually formulated in the form of its hydrochloride), and diltiazem or the betablocker metoprolol (usually formulated as the tartrate).

The water soluble salts of polyuronic acids suitable for use herein includes water-soluble salts of alginic acids, for example, forms which are high in guluronic acid such as sourced from Laminaria Digitata, forms which are high in mannuronic acid such as sourced from Ascophyllum Nodosum, and mixed forms from algal sources, as well as water-soluble salts of pectic acid, that is polygalacturonic acid.

The amount of a salt of a polyuronic acid that will be present will depend upon the pharmaceutical present and could range up to less than about 50% by weight of the powder formulation. Usually, the salt of the polyuronic acid will be present in an amount within the range of from about 15 to about 45% by weight and preferably from about 20 to about 40% by weight of the formulation. Such salt will preferably take the form of a salt of alginic acid, such as an alkali metal salt such as sodium alginate or potassium alginate or ammonium alginate, and preferably sodium alginate. The salt of alginic acid will have a viscosity of up to about 500 or more centipoises in 1% solution at 25° C. and preferably from about 5 to about 350 centipoises. It will be appreciated that mixtures of the same or different alginic acid salts of the same or different viscosities may be employed herein.

The polyuronic acid salt will be employed in a weight ratio to the hydrocolloid gelling agent of within the range of from about 0.1:1 to about 10:1 and preferably from about 0.4:1 to about 8:1.

The hydrocolloid gelling agent, may be of the compressible or non-compressible type, and is essential to the practice of the invention in that it absorbs water, swells and forms a gelatinous layer. It will be of the type to provide a viscosity of 50 to 100,000 centipoises in a 2% aqueous solution at 20° C., will have a molecular weight ranging from about 80,000 to about 300,000. Thus, the hydrocolloid is provided in an amount of up to about 35% by weight of the formulation and preferably from about 3 to about 15%.

The hydrocolloid for use in the powder formulation of the invention will have a viscosity of more than 50 centipoises as indicated above, and will preferably comprise cellulose polymers which are cellulose ethers such as methyl cellulose, cellulose alkyl hydroxylates such as hydroxypropylmethyl cellulose, hydroxypropyl cellulose, hydroxymethyl cellulose or hydroxyethyl cellulose, cellulose alkyl carboxylates such as carboxymethyl cellulose and carboxyethyl cellulose, and alkali metal salts of cellulose alkyl carboxylates, such as sodium carboxymethyl cellulose and sodium carboxyethyl cellulose, as well as carboxypolymethylene (molecular weight 2.5 to 3.5 million). Preferred are sodium carboxymethyl cellulose, methyl cellulose, hydroxypropylmethyl cellulose and carboxypolymethylene. However, it is to be understood that any hydrocolloid may be employed in the present invention, such as, for example, gum acacia, guar gum, gum tragacanth, gum xanthan, an alkali metal carageenate, or mixtures thereof.

Other examples of suitable hydrocolloids are set out in Sheth et al. U.S. Pat. No. 4,140,755.

The sustained release powder will also include additional edible non-toxic ingredients as conventionally employed powder medicinal dosage forms. Thus, the powder of the invention may include one or more excipients in conventional amounts, such as lactose, sugar, microcrystalline cellulose, wood cellulose, mannitol, sorbitol, one or more lubricants in an amount within the range of from about 0.25 to about 8% by weight of the powder, and preferably from about 0.5 to about 5% by weight of the powder, such as magnesium stearate, stearic acid, palmitic acid, talc, carnauba wax and the like. Other conventional ingredients which may optionally be present include preservatives, stabilizers, antiadherents or silica flow conditioners or glidants, such as Syloid brand silicon dioxide as well as FD&C colors.

The powder of the invention may be loaded into conventional capsules, such as hard gelatin capsules, to form the finished formulation of the invention.

Preferred controlled release powder formulations of the invention will include the following:

| Ingredient | % by Weight |
|---|---|
| Medicament (basic) (e.g., verapamil) | 20 to 60 |
| Alginic acid basic salt (such as Na alginate - viscosities ranging from 5 to 350 at 20° C. in 1% solution) | 15 to 45 |
| Hydrocolloid gelling agent (such as hydroxypropylmethyl cellulose, e.g., Methocel E4M, viscosity of 4000 cps at 2% solution at 20° C.) | 3 to 15 |
| Excipients | qs to 100% |
| Average particle size | 50 to 400μ |
| Bulk density | 0.15 to 0.55 g/cm³ |

Figure 1:
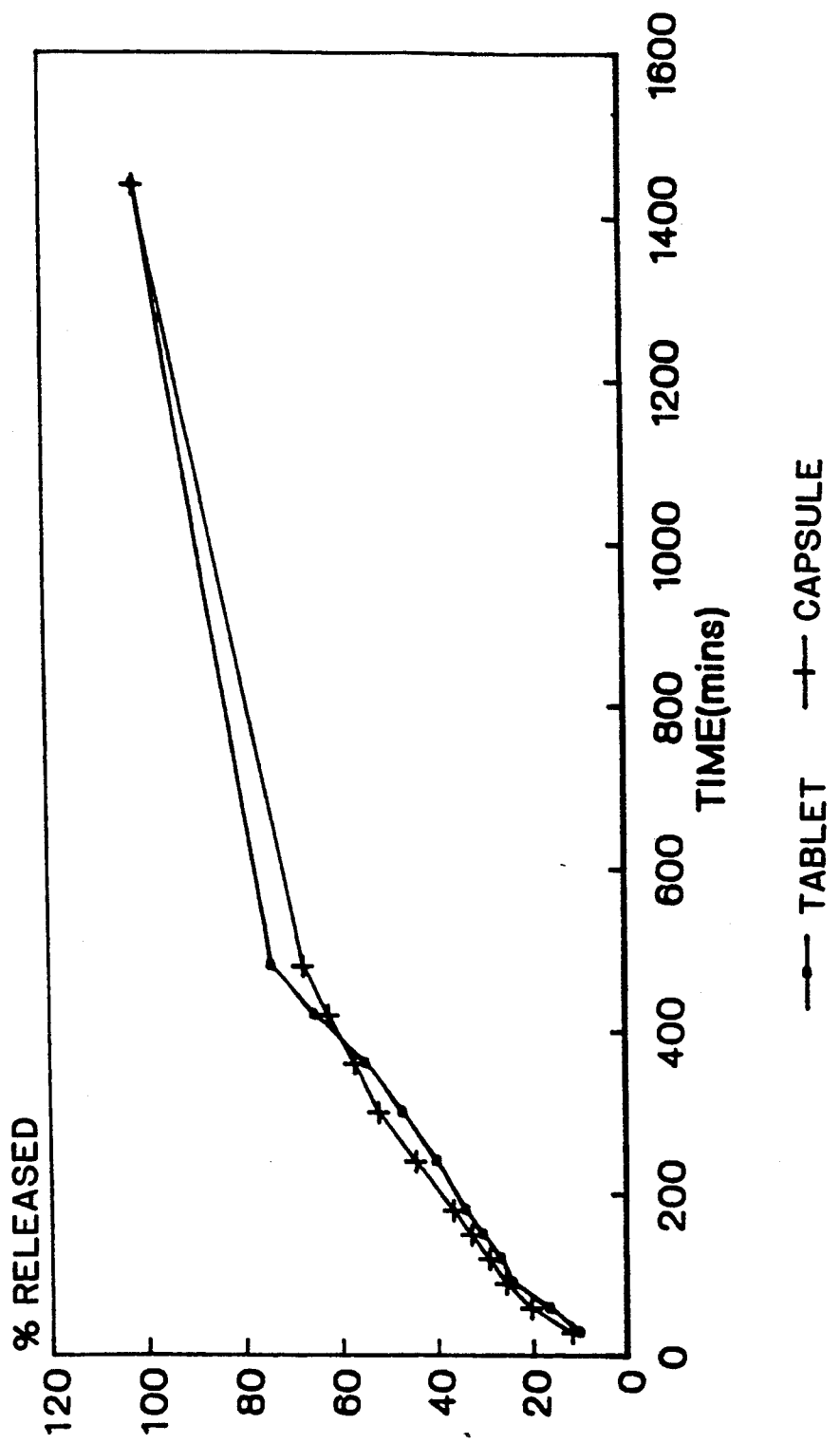
FIG. 1 is a graph showing verapamil dissolution profiles for tablet and powder floating capsule at 50 rpm basket speed (pH 1, 0-1 hr.; pH 7.5, 1-12 hr.)

The following Examples represent preferred embodiments of the present invention.

EXAMPLE 1

A buoyant sustained release powder formulation capable of slowly releasing the calcium channel blocker verapamil HCl in vitro regardless of the pH of the environment for a period of up to 10 to 12 hours or more and having the following composition was prepared as described below.

| Ingredient Powder Composition | Per Dosage Unit (mg) |
|---|---|
| Verapamil hydrochloride | 240 |
| Sodium alginate (300 cps) | 135 |
| Hydroxypropylmethyl cellulose (Methocel E4M viscosity of 4000 cps (hydrophilic polymer) | 25.2 |
| Avicel pH 101 (microcrystalline cellulose) | 40.8 |
| Lactose | 8.3 |
| Hydroxypropylmethyl cellulose (binder - Methocel E5) | 4.5 |
| Magnesium stearate (lubricant) | 4.5 |

The verapamil raw material was first screened through a 40# sieve before the required amount for manufacture was weighed. All other excipients were screened through a 20# sieve prior to weighing. The accurately weighed powders were gradually triturated into a suitable jar which was subsequently blended for 10 minutes in a turbula mixer. Approximately 450 mg of the blended material (about 250μ average particle size and bulk density of about 0.3 g/cm³) was then filled into size 0 grey hard gelatin capsules and the fill weights accurately recorded.

The following materials and methods were employed in testing the above capsules.

A. Materials

1) USP XXI Simulated Intestinal Fluid without Enzymes (SIF)

6.8 g of anhydrous potassium dihydrogen orthophosphate ($KH_2PH_4$) was dissolved into distilled water and added to a 1000 ml graduated cylinder. To this solution 190 ml of 0.2 M sodium hydroxide solution and a further 400 ml of distilled water were added. The solution was mixed thoroughly, the pH adjusted to 7.5±0.1 using 0.2 M sodium hydroxide and then diluted to the 1000 ml mark with distilled water.

2) USP XXI Hydrochloric Acid 8.8 ml of concentrated hydrochloric acid (S.G 1.18) was added to a 1000 ml graduated cylinder containing 800 ml of distilled water. The solution was then diluted to the 1000 ml mark with distilled water and mixed thoroughly.

3) Verapamil HCl Standard Solution In 0.1 M Hydrochloric Acid

Into a 1000 ml volumetric flask approximately 240 mg of verapamil HCl was accurately weighed. This was dissolved in 5.00 ml of methanol, diluted to volume with 0.1 M HCl and then mixed thoroughly.

In SIF The above was repeated but using SIF.

4) Verapamil Tablets

For comparison of release profiles, an experimental verapamil HCl 240 mg SR tablet was used. The tablet formulation is given in Table 1.

TABLE 1

| Formula of In-House Generic Verapamil SR Tablet | |
|---|---|
| Raw Material | mg/450 mg Tablet |
| Verapamil HCl | 240.00* |
| Methocel E4M | 25.20 |
| Manucol DMF | 135.00 |
| Avicel PH 101 | 40.80 |
| Methocel E5 | 4.50 |
| Magnesium Stearate | 4.50 |
| Total | 450.00 |
| Sepifilm 003 | 7.35 |
| Sepisperse AP3149 | 6.15 |

* Quantities shown assume 100% potency of verapamil HCl

B. Equipment

1) Dissolution Apparatus

The rotating basket apparatus. In this test, the caleva multiple spindle model 7ST (G. B. Caleva Ltd., Dorset) was used, equipped with a temperature controlled water bath (37°±0.5° C.) and 1000 ml round bottom pyrex glass dissolution vessels fitted with lids and sample tubes.

2) Disintegration Apparatus

The Erweka 4 basket rack assembly model ZT2 (F. Copley and Sons, Nottingham) was used. This machine consisted of 4 basket rack assemblies which lowered and raised at a rate of 29 to 32 cycles/minute into the immersion fluid which was contained within a low form beaker at a temperature of between 35° and 39° C.

3) Spectrophotometer

The Hewlett Packard 8452A Diode Array Spectrophotometer equipped with a 1 cm quartz cell was used to obtain all spectroscopic data. This is a single beam machine with one compartment for a reference/sample cell.

C. Experimental

1) Preparation of Powder Filled Verapamil HCl 240 mg SR Capsules

Capsules were prepared from the tablet formulation excluding the coating materials (Table 2).

TABLE 2

| Basic Formulation Used to Produce Capsules | |
|---|---|
| Raw Material | mg/450 mg Capsule |
| Verapamil HCl | 240.00 |
| Methocel E4M | 25.20 |
| Manucol DMF | 135.00 |
| Avicel PH 101 | 40.80 |
| Methocel E5 | 4.50 |
| Magnesium Stearate | 4.50 |

D. In-vitro Dissolution Test for Verapamil HCl 240 mg SR Tablets and Capsules Each of the six glass dissolution vessels were filled with 1000 ml of 0.1 M HCl and brought to 37°±0.5° C. using the temperature controlled water bath. The medium was then deaerated with helium and the temperature allowed to re-equilibrate. One sample of the dosage form under investigation was placed into each basket and the test initiated by lowering the baskets into the dissolution vessels and rotating them at the pre-determined speed (50 or 100 rpm).

At 30 and 60 minutes, 10 ml samples were filtered through the 0.45 micron disposable filters discarding the first 3 ml of filtrate; samples were then assayed for verapamil using the diode array spectrophotometer operating at an analytical wavelength of 260 nm and a reference wavelength of 320 nm.

Immediately after the 60 min. time point in 0.1 M HCl, the baskets were raised out of the dissolution vessels. Each vessel was emptied, rinsed, dried and then filled with exactly 1000 ml of SIF and brought to 37°±0.5° C. using the temperature controlled water bath. The medium was then deaerated with helium and the temperature allowed to re-equilibrate. The baskets were then re-lowered and the dissolution continued with 10 ml samples being removed using plastic syringes 30, 60, 90, 120, 180, 240, 300, 360, 420 and 1380 minutes after re-starting the dissolution. The samples were filtered through the 0.45 micron disposable filters discarding the first 3 ml of filtrate. Samples were then assayed for verapamil HCl using the Diode Array Spectrophotometer operating at an analytical wavelength of 260 nm and a reference wavelength of 320 nm. The spectroscopic data was calculated to determine the percent dissolution profile.

E. In-vitro Dissolution Test for Verapamil HCl 240 mg SR Dosage Forms Using a Single Medium (0.1 M HCl or SIF)

Using the conditions already described in section D, dissolution tests and sample assay were performed upon the various dosage forms except that instead of employing a switch of media after 1 hour, the same media was used throughout the investigation.

F. In-vitro Test for Verapamil Release from Verapamil HCl 240 mg SR Tablets and Capsules Utilizing Disintegration Apparatus Each of the four glass, flat bottomed vessels were filled with 500 ml of 0.1 M HCl and brought to 36°±0.5° C. using the temperature controlled water bath. One sample of the dosage form under investigation was placed into a single sample tube of each rack assembly. The experiment was initiated by switching on the machine and the rack assemblies were plunged repeatedly into and out of the medium at a rate of approximately 30 cyc/min.

10 ml samples were withdrawn from each vessel in a plastic syringe after 5, 10, 15, 30, 60 and 120 minutes. The samples were filtered through 0.45 micron disposable filters and analyzed and calculated as before.

Results and Discussion

Surprisingly, when the loose powder filled capsule formulation was exposed to the pH switching dissolution experiment (Section D) the release profile obtained was found to be similar to that of the tablet (FIG. 1—pH switched at 1 hour). It was also noticed that the capsules rose to the top of the baskets during the experiment, i.e., the capsules exhibited buoyant properties.

It would appear that the capsule shell serves to retain the powder plug initially, however, as fluid penetrates in through the gelatin shell into the device, the polymers present hydrate to form a viscous gel layer around the dry inner core.

Figure 2:
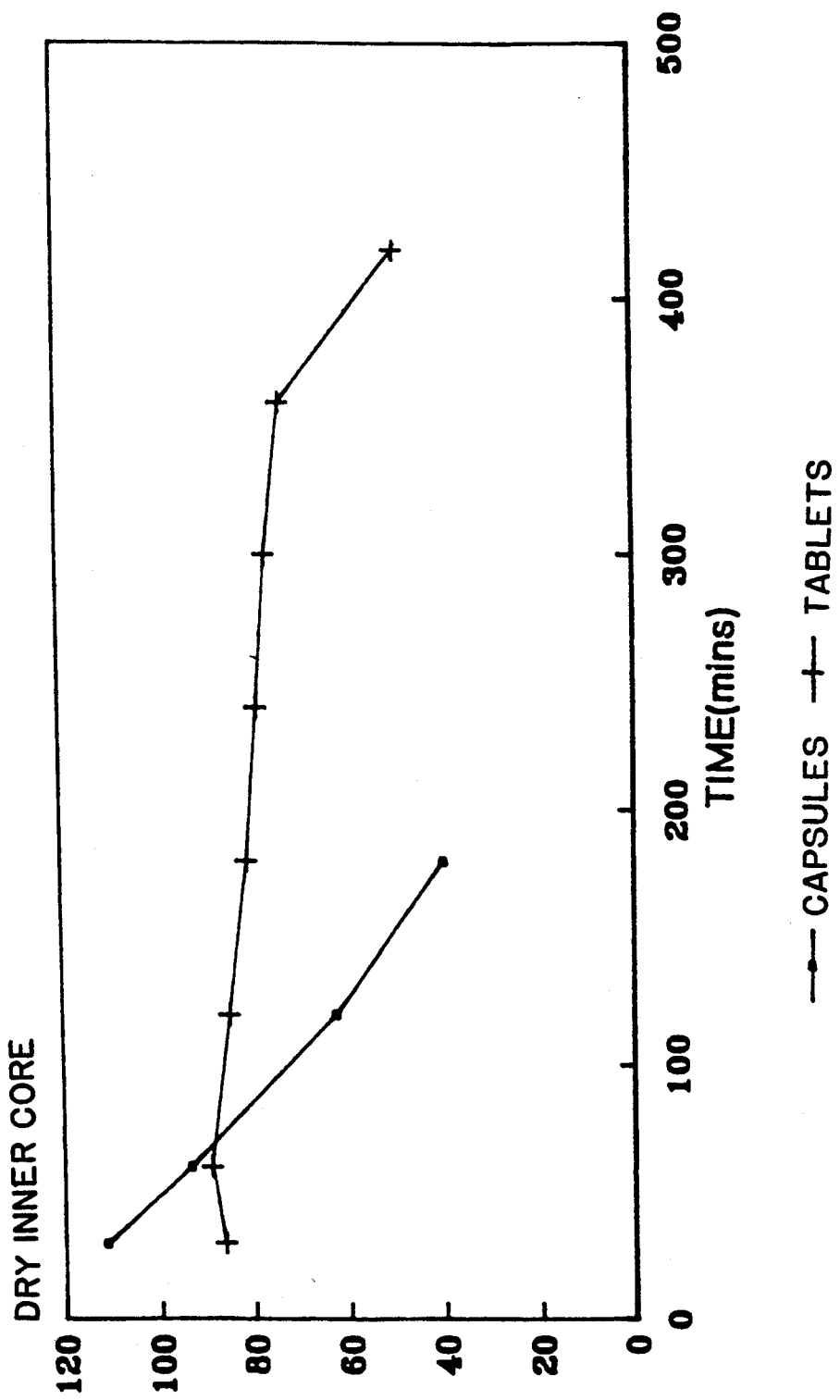
FIG. 2 is a graph showing rate of fluid penetration into tablet and floating capsule in 0.1 M HCl.
Figure 3:
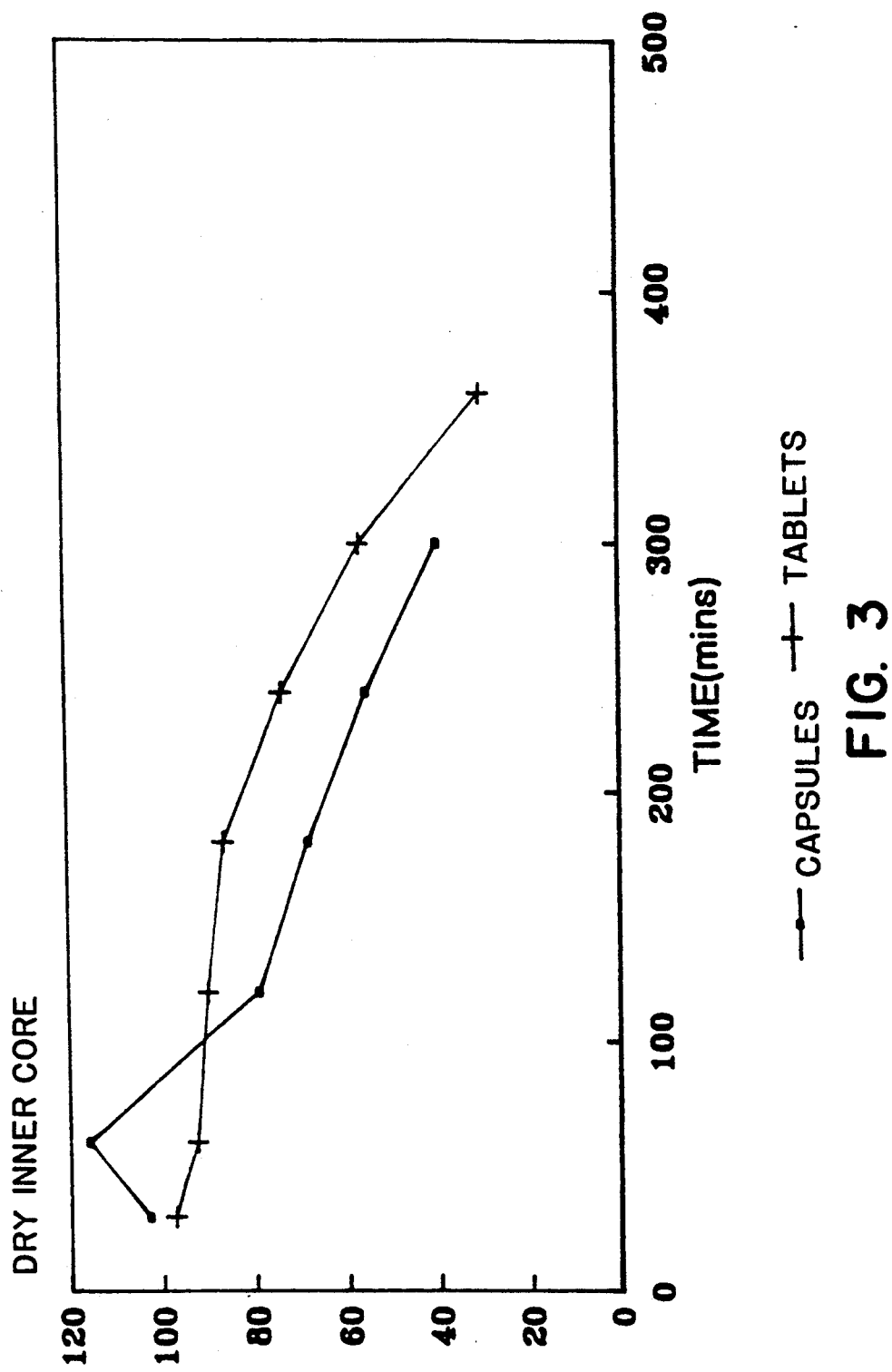
FIG. 3 is a graph showing rate of fluid penetration into tablet and floating capsule in S.I.F. (pH 7.5)

The capsules buoyancy may be attributed to the powder blends low bulk density (0.35 gcm$^3$). Studies have shown that the capsules are capable of floating for up to 5 hours in 0.1 M HCl. By this time, it is envisaged that sufficient fluid has penetrated into the device so as to remove enough air from the capsule core that the dosage form's density rises above that of the immersion fluid. Studies conducted into the penetration rate of fluid into the two devices are presented in FIGS. 2 and 3 (where dry inner core is expressed as a % of initial diameter). These diagrams show that the processes are essentially different between the two dosage forms and also between the two media. Overall, there appears to be a greater rate of fluid penetration into the capsule which is perhaps predictable due to its greater porosity. It is also noteworthy that the capsule seemingly experiences an initial expansion in the diameter of its dry inner core.

Since the water penetration rates do in fact appear to be different, it would infer that this mechanism is of only minor importance to the rate of verapamil release since these have been shown to be very similar in nature.

Following oral administration, the device would inevitably be exposed to more violent stresses in the gastro intestinal tract than those experienced at 50 rpm in dissolution apparatus. It is therefore pertinent to investigate how the capsules release properties compare to those of the tablet under more vigorous conditions.

Figure 4:
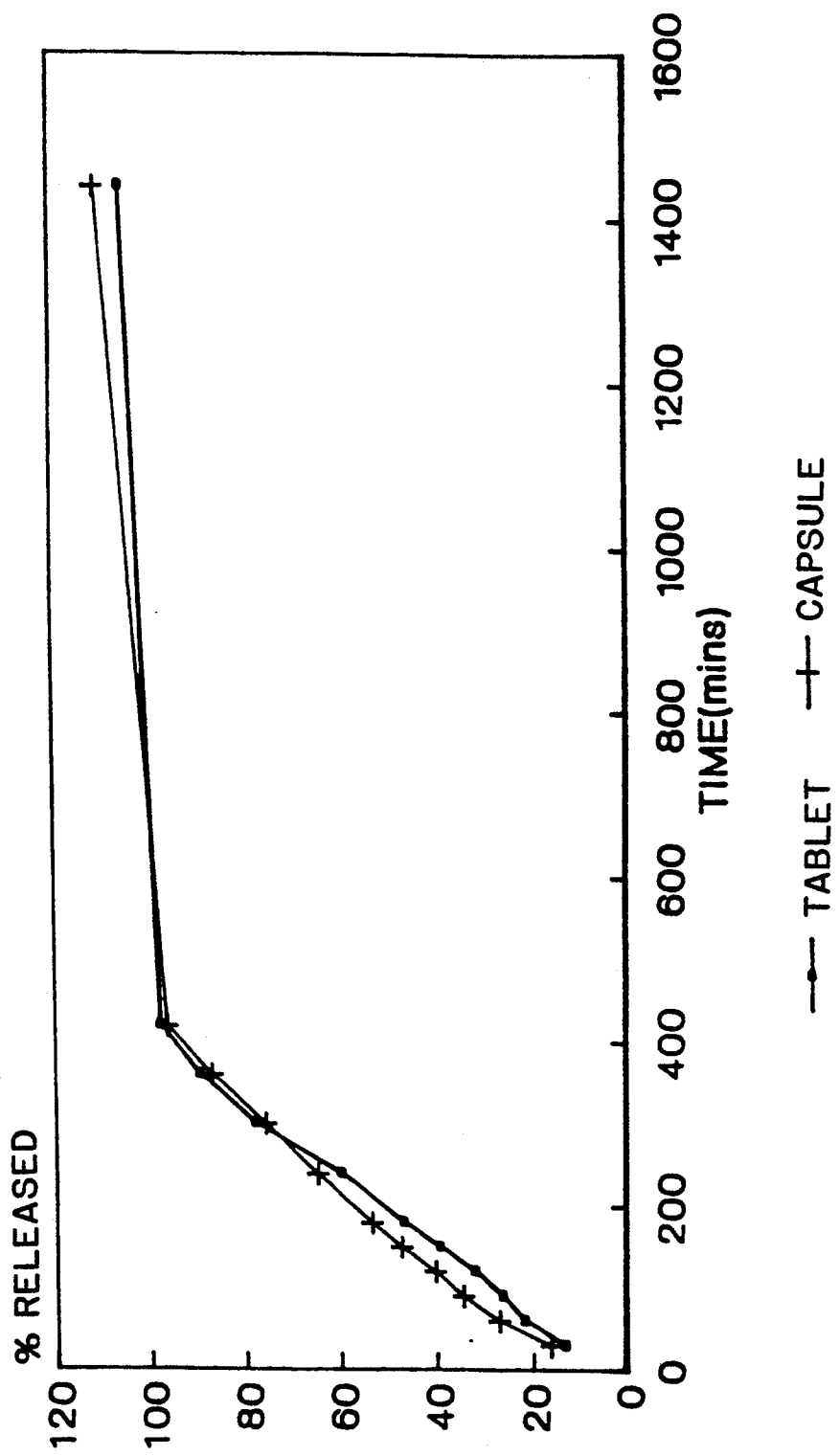
FIG. 4 is a graph showing verapamil dissolution profiles for tablet and powder floating capsule at 100 rpm basket speed (pH 1, 0-1 hr., pH 7.5, 1-12 hr.)
Figure 5:
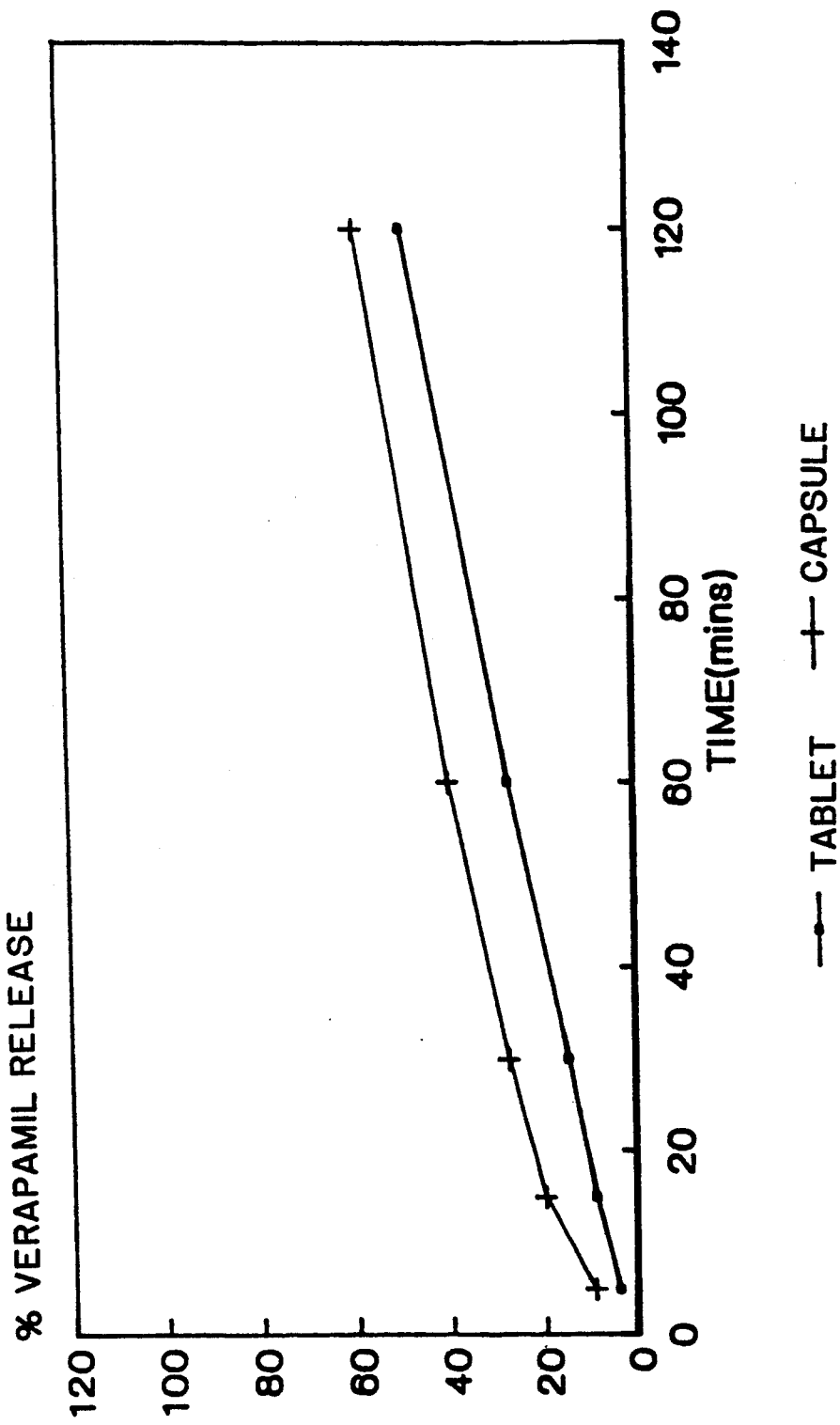
FIG. 5 is a graph showing verapamil dissolution profile for tablet and powder floating capsule using disintegration apparatus.
Figure 6:
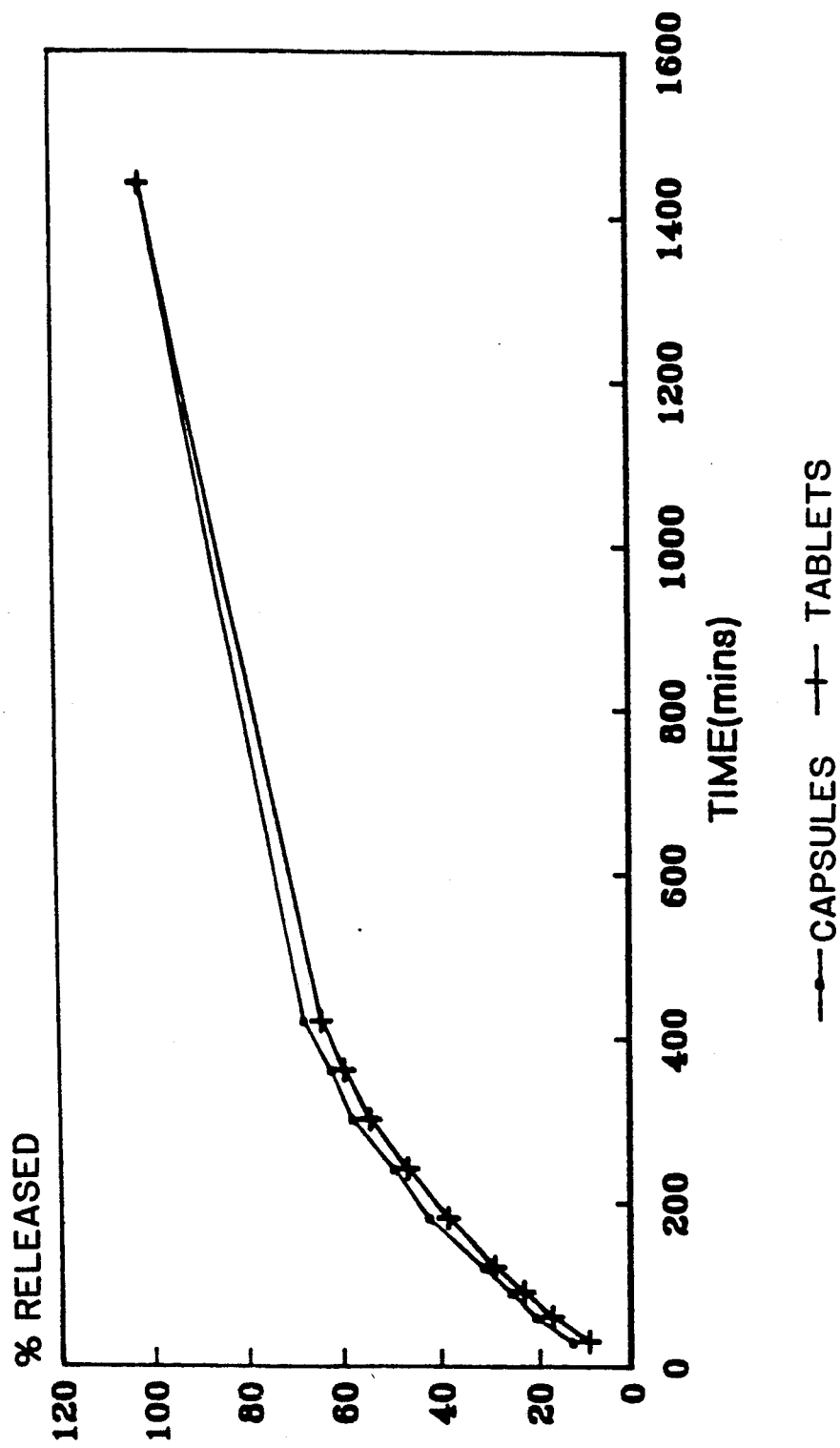
FIG. 6 is a graph showing verapamil dissolution profiles for tablets and powder floating capsules in 0.1 M HCl at basket speed of 50 rpm.

FIG. 4 shows that at a basket rotation speed of 100 rpm (pH switched at 1 hour), the two devices once again exhibit similar release profiles. The rate of drug release is increased by approximately the same amount in the two dosage forms. This greater rate of drug release may be attributed to factors such as more rapid diffusion of drug out of the matrix and increased erosion of the device. The former effect would arise due to the smaller diffusion layer thickness and the latter effect due to increased frictional forces on the device. Under the conditions present within disintegration apparatus, there is a greater initial burst in verapamil release from the capsule formulation, however, the release rates then appear to become very similar in nature over the two hour test period (FIG. 5; experiment performed in 0.1 M HCl).

EXAMPLE 2

A buoyant propranolol powder capsule in accordance with the present invention is prepared following the procedure of Example 1 except substituting propranolol for the verapamil hydrochloride.

EXAMPLE 3

A buoyant trifluoperazine HCl powder capsule in accordance with the present invention is prepared following the procedure of Example 1 except substituting trifluoperazine HCl for the verapamil hydrochloride.

EXAMPLE 4

A buoyant diltiazem HCl powder capsule in accordance with the present invention is prepared following the procedure of Example 1 except substituting diltiazem HCl for the verapamil hydrochloride.

It will be understood that with respect to the formulations prepared in Examples 2, 3 and 4, the ratio of HPMC/alginate and viscosity grade of alginate may be modified to yield drug release more or less independent of environmental pH, consistent with the in vivo needs of the product.

EXAMPLE 5

A buoyant metoprolol tartrate salt powder capsule in accordance with the present invention is prepared following the procedure of Example 1 except substituting metoprolol tartrate for verapamil hydrochloride.

EXAMPLE 6

A buoyant verapamil powder capsule containing sodium alginates of different viscosities having the following composition was prepared as described in Example 1.

| Ingredient | Amount/Powder capsule mg |
|---|---|
| Verapamil HCl | 240 |
| Sodium alginate 9 cps (measured at 20° C. in 1 solution) | 90 |
| Sodium alginate 300 cps (measured at 20° C. in 1% solution) | 45 |
| Hydroxypropylmethylcellulose 4000 cps (E4M) | 45 |
| Hydroxypropylmethyl cellulose 5 cps (E5) | 9 |
| Microcrystalline cellulose | 33.2 |
| Lactose BP | 8.3 |
| Magnesium stearate | 4.5 |
| | 450.0 mg |

The powder has a 250μ average particle size and a bulk density of 0.35 g/cm$^3$.

What is claimed is:

1. A buoyant controlled release pharmaceutical formulation in the form of a powder filled capsule from which a pharmaceutical of a basic character is released at a controlled rate irrespective of the pH of the environment, comprising a pharmaceutical of a basic character, a pH-dependent polymer which is a water-soluble salt of a polyuronic acid, in an amount of up to about 45% by weight of the formulation; a pH-independent hydrocolloid gelling agent having a viscosity of from about 50 to about 100,000 centipoises in 2% solution at 20° C., in an amount within the range of up to about 35% by weight of the formulation, and binder, said formulation being free of calcium on and carbon dioxide producing material and will float in gastric juices and which will have drug release properties similar to a tablet of similar composition.

2. The formulation as defined in claim 1 having a bulk density of within the range of from about 0.1 to about 0.8 g/cm$^3$.

3. The formulation as defined in claim 1 having an average particle size of within the range of fm about 25 to about 1000 μm.

4. The formulation as defined in claim 1 wherein the pH-dependent salt of a polyuronic acid is employed in a weight ratio to the pH-independent hydrocolloid gelling agent of within the range of from about 01:1 to about 10:1.

5. The formulation as defined in claim 1 wherein said pH-dependent salt of a polyuronic acid is employed in an amount within the range of from about 15 to about 45% by weight of the formulation and the pH-independent hydrocolloid gelling agent is employed in an amount within the range of from about 5 to about 20% by weight of said formulation.

6. The formulation as defined in claim 1 wherein said pharmaceutical of a basic character is employed in an amount of up to about 75% by weight of said formulation.

7. The formulation as defined in claim 1 wherein said pharmaceutical of a basic character is verapamil hydrochloride, said salt of alginic acid is sodium alginate, said hydrocolloid gelling agent is hydroxypropylmethyl cellulose having a viscosity of from about 50 to about 100,000 centipoises, said binder is hydroxypropylmethyl cellulose having a viscosity of from about 5 to about 15 centipoises.

8. The formulation as defined in claim 1 wherein said pharmaceutical of a basic character is a calcium antagonist.

9. The formulation as defined in claim 8 wherein said calcium antagonist is a salt of verapamil, a salt of diltiazem, a salt of nicardipine, a salt of nifedipine, a salt of gallapomil or a salt of cinnarizine.

10. The formulation as defined in claim 1 wherein said pharmaceutical of a basic character is a beta blocker, antihistamine, sympathomimetic, beta adrenergic agonist or bronchodilator, or central nervous system drug.

11. The formulation as defined in claim 10 wherein said beta blocker is a salt of propranolol, a salt of metoprolol, or a salt of nadolol, said antihistamine is a salt of chlorpheniramine, a salt of diphenhydramine, said sympathomimetic is a salt of phenylpropanolamine or a salt of pseudoephedrine, said beta adrenergic agonist is a salt of albuterol, fenoterol, or a salt of terbutaline, and said central nervous system drug is a salt of thioridazine, a salt of trifluoperazine, chlorpromazine, BMS 181101 BMY 14,802, buspirone, nefazadone, gepirone, tiospirone.

12. The formulation as defined in claim 1 wherein said hydrocolloid gelling agent is hydroxypropylmethyl cellulose, methyl cellulose, hydroxypropyl cellulose, or a mixture of two or more of such hydrocolloid gelling agents.

13. The formulation as defined in claim 1 wherein said salt of a polyuronic acid is a salt of alginic acid.

14. The formulation as defined in claim 13 wherein said salt of alginic acid is sodium alginate or potassium alginate.

15. The formulation as defined in claim 13 wherein the salt of alginic acid has a viscosity of within the range of from about 4 to about 300 centipoises in 1% solution at 25° C.

16. The formulation as defined in claim 13 containing alginic acid salts of two different viscosities.

17. In a controlled release pharmaceutical formulation from which a pharmaceutical of a basic character is released at a controlled rate irrespective of the pH of the environment, which includes a pharmaceutical of a basic character; a pH-dependent polymer which is a water-soluble salt of a polyuronic acid, in an amount of up to about 45% by weight of the formulation; a pH-independent hydrocolliod gelling agent having a viscosity within the range of from about 50 to about 100,000 centipoises in 2% solution at 20° C., in an amount of up to about 35% by weight of the formulation; and binder, said formulation being free of calcium ion and carbon dioxide producing material, the improvement which comprises the said formulation being in the form of a free-flowing powder filled capsule which is buoyant so that it will float in gastric juices and will have drug release properties similar to a tablet of similar composition.

18. The formulation as defined in claim 17 wherein the salt of a polyuronic acid is a salt of alginic acid.

19. The formulation as defined in claim 17 wherein the pH-dependent salt of a polyuronic acid is employed in a weight ratio to the pH-independent hydrocolloid gelling agent of within the range of from about 0.1:1 to about 10:1.

20. The formulation as defined in claim 17 wherein said pH-dependent salt of a polyuronic acid is employed in an amount within the range of from about 15 to about 45% by weight of the formulation and the pH-independent hydrocolloid gelling agent is employed in an amount within the range of from about 5 to about 20% by weight of said formulation.

21. The formulation as defined in claim 17 wherein said pharmaceutical of a basic character is employed in an amount of up to about 75% by weight of said formulation.

22. The formulation as defined in claim 17 having a bulk density of within the range of from about 0.1 to about 0.8 g/cm$^3$.

23. The formulation as defined in claim 17 having an average particle size of within the range of from about 25 to about 1000 μ.

* * * * *

UNITED STATES PATENT AND TRADEMARK OFFICE
CERTIFICATE OF CORRECTION

PATENT NO. : 5,169,638

DATED : December 8, 1992

INVENTOR(S) : Andrew Dennis et al

It is certified that error appears in the above-identified patent and that said Letters Patent is hereby corrected as shown below:

Column 11, line 11, "bn" should read --ion--.

Column 11, line 19, "fm" should read --from--.

Signed and Sealed this

Twenty-third Day of November, 1993

Attest:

BRUCE LEHMAN

Attesting Officer

Commissioner of Patents and Trademarks